United States Patent
Nakatsuka et al.

(10) Patent No.: US 9,345,646 B2
(45) Date of Patent: May 24, 2016

(54) DENTAL VISIBLE-LIGHT CURABLE COMPOSITION AND METHOD OF IDENTIFYING PRESENCE OF SAME

(71) Applicant: SHOFU INC., Kyoto (JP)

(72) Inventors: Toshiyuki Nakatsuka, Kyoto (JP); Kazuya Shinno, Kyoto (JP); Akihiro Nagafuji, Kyoto (JP); Shingo Tateishi, Kyoto (JP)

(73) Assignee: SHOFU INC., Kyoto-Shi (JP)

( * ) Notice: Subject to any disclaimer, the term of this patent is extended or adjusted under 35 U.S.C. 154(b) by 10 days.

(21) Appl. No.: 14/060,934

(22) Filed: Oct. 23, 2013

(65) Prior Publication Data

US 2014/0120499 A1 May 1, 2014

(30) Foreign Application Priority Data

Oct. 24, 2012 (JP) .................................. 2012-248818
Oct. 11, 2013 (JP) .................................. 2013-214047

(51) Int. Cl.
*A61K 6/00* (2006.01)
*A61K 6/083* (2006.01)

(52) U.S. Cl.
CPC .............. *A61K 6/002* (2013.01); *A61K 6/0023* (2013.01); *A61K 6/0061* (2013.01); *A61K 6/0097* (2013.01); *A61K 6/083* (2013.01)

(58) Field of Classification Search
CPC .................. A61C 2201/002; A61K 6/0061
See application file for complete search history.

(56) References Cited

U.S. PATENT DOCUMENTS

| | | | |
|---|---|---|---|
| 6,747,406 B1* | 6/2004 | Bortscheller et al. | 313/512 |
| 8,969,812 B2* | 3/2015 | Yoshikawa et al. | 250/361 R |
| 2006/0194172 A1* | 8/2006 | Loveridge | 433/215 |
| 2008/0157113 A1* | 7/2008 | Hayashi | 257/98 |
| 2010/0297588 A1* | 11/2010 | Kalgutkar et al. | 433/228.1 |
| 2011/0062873 A1 | 3/2011 | Gall et al. | |
| 2011/0200971 A1* | 8/2011 | Kalgutkar et al. | 433/201.1 |
| 2012/0012789 A1* | 1/2012 | Yamada et al. | 252/301.6 R |

FOREIGN PATENT DOCUMENTS

| | | |
|---|---|---|
| EP | 0389239 | 9/1990 |
| EP | 1245548 | 10/2002 |
| JP | 02-233605 | 9/1990 |
| JP | 2005-041825 | 2/2005 |
| JP | 2009-510120 | 3/2009 |
| JP | 2011-184402 | 9/2011 |
| JP | 2012-505889 | 3/2012 |
| WO | 2007/041477 | 4/2007 |
| WO | 2010/045096 | 4/2010 |

OTHER PUBLICATIONS

European Search Report dated Jan. 16, 2015, 5 pages.

* cited by examiner

*Primary Examiner* — Ralph Lewis
(74) *Attorney, Agent, or Firm* — Rankin, Hill & Clark LLP

(57) ABSTRACT

A dental curable composition that allows easily identifying the presence of the dental curable composition in an oral cavity is provided. A dental visible-light curable composition contains a fluorescent substance that generates fluorescence when irradiated with visible light. The fluorescent substance is a compound of formula $A_3B_2C_3O_{12}$ containing Ce, absorbs visible light with a peak wavelength in a wavelength range of 380 to 500 nm, and generates fluorescence with a peak wavelength in a wavelength range of 550 to 780 nm. In formula $A_3B_2C_3O_{12}$, A, B, and C are a dodecahedral eight-coordinate Y element, an octahedral six-coordinate Al element, and a tetrahedral four-coordinate Al element, respectively.

6 Claims, No Drawings

DENTAL VISIBLE-LIGHT CURABLE COMPOSITION AND METHOD OF IDENTIFYING PRESENCE OF SAME

TECHNICAL FIELD

The present invention relates to a dental visible-light curable composition for use in the dental field such as a dental crown material, a filling material, a prosthetic material, an adhesive material, and a preventive material, and in particular to a dental visible-light curable composition having fluorescent visual recognizability that generates fluorescence when irradiated by a visible-light source. The present invention also relates to a method of identifying the presence of a dental visible-light curable composition having fluorescent visual recognizability by irradiation with visible light or a visible ray from a visible light source.

BACKGROUND ART

In recent years, aesthetic dental treatment has been drawing attention in the dental field, and a restorative procedure in which a dental material having high aesthetics for a color tone that is similar to that of natural teeth has been put into practice. In such circumstances, a dental curable composition called a "composite resin" composed of a polymerizable monomer, a filler, a polymerization initiator, and so forth is clinically most heavily used as a material for restoring a chipped portion of a tooth from the viewpoint of operability, mechanical properties, and aesthetics. Clinical application of the material is very satisfactory from the viewpoint of aesthetics because the material enables aesthetic restoration in which the color tone of the restored portion is so similar to that of the tooth substance that the restored portion is indistinguishable from the natural teeth after filling the chipped portion. Meanwhile, the natural teeth have fluorescence properties to generate fluorescence when irradiated with an ultraviolet ray and to turn pale under black light. Unlike the natural teeth, however, the dental curable composition originally does not have fluorescence properties. Therefore, when an object restored using the composition is seen under an ultraviolet ray or black light, the object may look darker than the surrounding teeth, which may degrade the aesthetic quality. Therefore, dental curable compositions containing various fluorescent substances for the purpose of exhibiting fluorescence properties that are similar to those of the tooth substance are proposed. For example, JP2012-505889A discloses a dental curable composition containing a fluorescent organic dye. JP2011-184402A discloses a composition containing a fluorescent substance formed from alumina particulates and a compound having a benzophenone skeleton. JP02-233605A discloses a composition containing 2,5-dihydroxy diethyl terephthalate. JP2009-510120A discloses a dental composition containing 7-diethylamino-4-methylcoumarin. JP2005-41825A discloses a dental material containing a fluorescent glass filler containing a rare-earth oxide. Such disclosed technologies have enabled dental curable compositions to look similar to the natural teeth when irradiated with light in an ultraviolet or near-ultraviolet range that is shorter in wavelength than visible light.

In recent years, in addition, explorations and diagnoses have been rendered important in dental treatment, and it has become necessary to check the clinical status and information on a portion to which a dental material is applied. In particular, dental compositions such as a fissure sealant applied to the tooth substance and an orthodontic adhesive remaining on the tooth surface after removal of a correcting bracket are required to be visually recognizable in order to grasp the status of the procedure or decide the next policy of the procedure by identifying the presence of such dental compositions. The dental compositions containing various fluorescent substances proposed earlier are characterized in that they look in the same way as the tooth substance both with the eyes and under irradiation with an ultraviolet ray or black light, and are found to be unsatisfactory from the viewpoint of visual recognizability to identify the presence of the dental compositions. Conversely, the visual recognizability of the dental compositions can be improved by having a fluorescent material having fluorescent chromogenic properties, which are completely different from those of the tooth substance, contained in the dental compositions. However, it is clearly not preferable in terms of biological safety to irradiate an oral cavity with an ultraviolet ray or black light in the course of an exploration or a diagnosis. Further, while it is possible to have a pigment with a color tone that is completely different from the color tone of the tooth substance contained in the dental compositions for the purpose of enhancing the visual recognizability with the eyes, this may result in degradation in aesthetics with the eyes.

There is further proposed a dental composition that can be visually recognized by irradiation with visible light or a visible ray by having a fluorescent substance that generates fluorescence by irradiation with visible light or a visible ray contained in the dental composition as in the invention taught in JP2005-41825A. In the dental composition taught in [0027], [0028], [0033] to [0035], and so forth of JP2005-41825A, a glass filler (fluorescent substance) containing $Eu_2O$ as a rare-earth oxide that generates fluorescence when irradiated with visible light or a visible ray is mixed in a visible light-curable composite resin. In the dental composition, however, the glass filler (fluorescent substance) containing at least 5 wt % of an oxide of Eu itself is mixed in an amount corresponding to a weight ratio of 3:1 based on the composite resin, and the content of the rare-earth oxide as the fluorescent substance to generate fluorescence may be too large. Because a large amount of the fluorescent substance is present in the dental composition, the dental composition may be colored by the fluorescent substance, which may degrade the aesthetics under natural light. If the content of the fluorescent substance is increased, the mechanical strength including the bending strength of the dental composition after being cured may be reduced, depending on the type of the fluorescent substance.

SUMMARY OF INVENTION

In view of the foregoing circumstances, it is an object of the present invention to provide a dental curable composition with fluorescent visual recognizability that can be distinguished from the tooth substance by irradiation with visible light in addition to maintaining certain levels of aesthetics when observed with the eyes and mechanical strength. It is further desirable to provide a method of identifying the presence of a dental curable composition by irradiation with visible light that is less harmful to living bodies in order to identify the presence of the dental curable composition.

In order to address the foregoing issue, the inventors made diligent studies, and found that in a dental visible-light curable composition containing a fluorescent substance that generates fluorescence when irradiated with visible light or a visible ray, a compound of formula $A_3B_2C_3O_{12}$ containing Ce that absorbs visible light or a visible ray with a peak wavelength in a wavelength range of 380 to 500 nm and generates fluorescence with a peak wavelength in a wavelength range of 550 to 780 nm is optimally used as the fluorescent substance contained in the dental visible-light curable composition. In the formula $A_3B_2C_3O_{12}$, A, B, and C are a dodecahedral eight-coordinate Y element, an octahedral six-coordinate Al element, and a tetrahedral four-coordinate Al element, respectively. The fluorescent substance is preferably the compound of formula $A_3B_2C_3O_{12}$ having a garnet structure and doped with Ce.

The dental visible-light curable composition containing the fluorescent substance absorbs visible light or a visible ray with a peak wavelength in a wavelength range of 380 to 500 nm, and generates fluorescence with a peak wavelength in a wavelength range of 550 to 780 nm. The fluorescence is sufficiently visually recognizable through an optical filter configured to block or interrupt light with a peak wavelength in a wavelength range of less than 550 nm. In other words, if the emitted visible light or visible ray has a peak wavelength in a wavelength range of 380 to 500 nm (a wavelength range for blue color), and the fluorescence generated by the fluorescent substance has a peak wavelength included in a wavelength range of 550 to 780 nm (a wavelength range for yellow color to red color), most of the emitted visible light or visible ray (a reflected portion of the emitted visible light or visible ray) is blocked or interrupted by an optical filter capable of blocking or interrupting (or cutting off) light with a peak wavelength in a wavelength range of less than 550 nm (a wavelength range including at least blue color), and the fluorescence generated by the dental curable composition containing the fluorescent substance is not blocked or interrupted by the optical filter but transmits the optical filter. The optical filter that can be used is not limited to optical filters that block or interrupt (or cut off) light with a peak wavelength in a wavelength range of less than 550 nm. That is, any optical filter that blocks or interrupts the peak wavelength of the emitted visible light or visible ray and that transmits the fluorescence generated from the fluorescent substance may be used.

If the fluorescent substance is contained in the dental visible-light curable composition, a dental curable composition with extremely high fluorescence properties for visible light used to cure the composition can be obtained. As a result, the presence of the dental curable composition in an oral cavity can be easily visually recognized using a visible-light irradiator configured to generate visible light for curing and an optical filter used to visually recognize the irradiation state during curing. This facilitates curing of the dental curable composition while identifying the presence of the dental curable composition. In particular, the presence of the dental curable composition can be identified even in circumstances where the presence of a small amount of the dental curable composition must be identified (e.g. for use for a fissure sealant or an orthodontic adhesive). Specifically, after pits and fissures are filled with the fissure sealant, it can be easily checked in regular checkups or the like whether the sealant is not peeled off or the like. For the orthodontic adhesive, which must be removed after an orthodontic treatment, such a small amount of the orthodontic adhesive remaining on the tooth surface that cannot be identified with the eyes can even be easily identified. Unlike the fluorescent substance according to the related art, the fluorescent substance used in the present invention can generate strong fluorescence if not contained in a large amount, and therefore the presence of the fluorescent substance does not affect the aesthetics and the mechanical strength of the dental curable composition. If the compound having a garnet structure and doped with Ce is contained in the dental visible-light curable composition as the fluorescent substance, the mechanical strength of the dental curable composition can be enhanced.

Specifically, in a dental treatment setting, a blue LED configured to emit light with a peak wavelength in a wavelength range of 380 to 500 nm (a wavelength range for blue color) is commonly used to cure the dental curable composition. Light with a peak wavelength included in a wavelength range of 380 to 500 nm (a wavelength range for blue color) is included in a short wavelength region that is close to an ultraviolet ray among the visible light or the visible ray. Thus, an optical filter configured to cut off light with a peak wavelength included in a wavelength range of less than 550 nm (a wavelength range including at least blue color) is used to protect the eyes of a worker. The worker identifies the presence of the dental curable composition through the optical filter. In contrast, the fluorescent substance used in the present invention can generate fluorescence with a peak wavelength included in a wavelength range of 550 to 780 nm (a wavelength range for yellow color to red color). Therefore, while a reflected portion of the visible light or the visible ray emitted from the blue LED is blocked or interrupted by the optical filter, the fluorescence generated by the dental curable composition containing the fluorescent substance is not blocked or interrupted by the optical filter. That is, because only the fluorescence emitted from the dental curable composition transmits the optical filter, the worker can identify only the fluorescence generated from the dental curable composition via the optical filter while curing the dental curable composition by irradiation from the blue LED. Thus, use of the dental curable composition according to the present invention allows reliably identifying the presence of the dental curable composition in an oral cavity using the existing devices.

The content of the fluorescent substance in the dental curable composition may be determined as desired as long as the presence of the dental curable composition in an oral cavity can be identified. If the content of the fluorescent substance exceeds 5.0 wt %, the dental curable composition strongly tends to be tinged with yellow after being cured, which may affect the aesthetics under natural light when seen with the eyes. If the content of the fluorescent substance is less than 0.01 wt %, meanwhile, the dental curable composition contains less fluorescence source, and therefore generates weaker fluorescence as a matter of course. Therefore, the content of the fluorescent substance is preferably determined to be 0.01 to 5.0 wt % to reliably identify the presence of the dental curable composition in an oral cavity without affecting the aesthetics under natural light.

There is further provided a method of distinguishing the dental curable composition according to the present invention from the tooth substance by irradiation with visible light that is less harmful to living bodies, that is, a method of identifying the presence of a dental visible-light curable composition containing a fluorescent substance that generates fluorescence when irradiated with visible light or a visible ray.

The method of identifying the presence of a dental curable composition includes: applying the dental visible-light curable composition according to the present invention discussed above (the dental visible-light curable composition containing a fluorescent substance that is a compound of the formula described above containing Ce, that absorbs visible light or a visible ray with a peak wavelength in a wavelength range of 380 to 500 nm, and that generates fluorescence with a peak wavelength in a wavelength range of 550 to 780 nm) into an oral cavity of a patient as the fluorescent substance contained in the dental curable composition. The method also includes: irradiating the oral cavity of the patient with the visible light or the visible ray; and viewing the fluorescence generated by the fluorescent substance through an optical filter to identify the presence of the dental visible-light curable composition. Conditions such as the structure, the properties, and the content of the fluorescent substance, the attribute and type of the emitted visible light or visible ray, and the function of the optical filter may be the same as the conditions adopted for the dental curable composition according to the present invention. By using the method of identifying the presence of a dental curable composition, it is possible to obtain the same effect as that obtained when the dental curable composition according to the present invention is used (that is, the effect that the dental curable composition in an oral cavity can be easily identified).

The present invention described above achieves the following effects.

The dental curable composition according to the present invention can be clearly distinguished from the tooth substance by irradiation with strong visible light by an irradiator without adversely affecting the aesthetics in an observation with the eyes and the mechanical strength. The presence of the dental curable composition according to the present invention can be identified by irradiation with visible light that is less harmful to living bodies. A light irradiator commonly used to cure a dental curable composition can also be used for irradiation with visible light, with no need for a special device therefor. In particular, use of a light irradiator including a blue LED with a peak wavelength in a wavelength range of 380 to 500 nm as the light source allows easily identifying the presence of the dental curable composition without using a special device, which is advantageous to dentists.

The present invention is superior from the viewpoint of the fluorescent chromogenic properties and various properties as discussed later. Further, when irradiating the dental curable composition according to the present invention with visible light to cure the dental curable composition, polymerization of the polymerizable monomer inside the dental curable composition according to the present invention is promoted to improve the curability, which improves the hardness and the bending strength in particular, because the dental curable composition contains a fluorescent substance that is a compound having a garnet structure and containing Ce that absorbs visible light.

DESCRIPTION OF EMBODIMENTS

An embodiment of the present invention will be described in detail below. A dental visible-light curable composition according to the present invention contains a fluorescent substance that generates fluorescence when irradiated with visible light or a visible ray. The fluorescent substance is formed from a compound of formula $A_3B_2C_3O_{12}$ containing Ce to generate fluorescence (exhibit fluorescence properties) when irradiated with visible light or a visible ray. In the example, a compound having a garnet structure and doped with Ce is used as the fluorescent substance. In addition, the fluorescent substance absorbs visible light or a visible ray with a peak wavelength in a wavelength range of 380 to 500 nm, and generates fluorescence with a peak wavelength in a wavelength range of 550 to 780 nm.

A in formula $A_3B_2C_3O_{12}$ is a dodecahedral eight-coordinate element (cation), and is considered to be at least one kind selected from Y, Sc, In, La, Ce, Pr, Nd, Pm, Sm, Eu, Gd, Tb, Dy, Ho, Er, Tm, Yb, and Lu. B in the formula is an octahedral six-coordinate element (cation), and is considered to be at least one kind selected from Al, Sc, Ga, Cr, In, La, Ce, Pr, Nd, Pm, Sm, Eu, Gd, Tb, Dy, Ho, Er, Tm, Yb, and Lu. C in the formula is a tetrahedral four-coordinate element (cation), and is considered to be selected from Al and Ga. O in the formula indicates oxygen as an element. In the example, a compound in which A in the formula is Y and B and C are each Al is used as the compound having a garnet structure. Other preferable examples of the compound having a garnet structure are considered to include a compound in which A, B, and C in the formula are Y, Al, and Gd, respectively, and a compound in which A, B, and C in the formula are Y, Al, and Ga, respectively.

In the embodiment, only Ce which generates fluorescence by irradiation with visible light is used as the element to be doped into the compound having a garnet structure, as a result of comprehensive evaluation of the aesthetics, the visual recognizability when irradiated with visible light, the processability for dentists, and the prevention of a reduction in mechanical strength due to addition of the fluorescent substance. Although use of fluorescent substances doped with rare-earth elements other than Ce was also considered, none of the other elements were found to meet all of the aesthetics, the visual recognizability when irradiated with visible light, the processability for dentists, and the prevention of a reduction in mechanical strength due to addition of the fluorescent substance.

In consideration of the effect on the material properties of the dental curable composition, the average grain size of the fluorescent substance is preferably in the range of 0.01 to 100.0 μm, more preferably in the range of 0.01 to 10.0 μm. The term "average grain size" as used herein means the median size based on volume as measured by a laser-diffraction grain size distribution-measuring device. The fluorescent substance may be processed into various shapes, and may be processed into the same shape as the shape of an organic filler, an organic-inorganic composite filler, or the like used as a filler, for example. The fluorescent substance may also be used as a colorant. The content of the fluorescent substance having a garnet structure and doped with Ce in the dental curable composition according to the present invention may be in such a range that the mechanical strength is not reduced and the presence of the dental curable composition in an oral cavity can be recognized when irradiated with visible light. The content of the fluorescent substance is preferably in the range of 0.001 to 5.0 wt % based on the entire dental curable composition in consideration of the effect on the fluorescence properties and the aesthetics, more preferably in the range of 0.01 to 5.0 wt % for higher identifiability of the dental curable composition, further more preferably in the range of 0.01 to 1.0 wt % in consideration of the mechanical strength of the dental curable composition.

The fluorescent substance having a garnet structure and doped with a rare-earth element (Ce) contained in the dental curable composition according to the present invention generates fluorescence by irradiation with visible light or a visible ray. The term "visible light or a visible ray" as used herein refers to a ray with a maximum absorption wavelength in a range of 380 nm to 780 nm, and any ray with an absorption wavelength distribution (wavelength range) including an ultraviolet, near-ultraviolet, near-infrared, or infrared region, which is outside the wavelength range discussed earlier, may be included in the visible light. The device for irradiation with visible light is not specifically limited. However, light irradiators formed from a halogen light source, an LED light source, or a plasma light source commonly used in the dental field to cure a composite resin or the like are preferably used, because no special device is required. Among such light irradiators, a light irradiator in which a blue LED with a peak wavelength included in a wavelength range of 380 to 500 nm is used as the light source is more preferably used.

The polymerizable monomer contained in the dental curable composition according to the present invention may be chosen from known monofunctional and polyfunctional polymerizable monomers commonly used in the dental field.

Typical examples of the polymerizable monomer generally suitably used include polymerizable monomers having an acryloyl group and/or a methacryloyl group. In the present invention, the terms "(meth)acrylates" and "(meth)acryloyls" are used to comprehensively express both acryloyl group-containing polymerizable monomers and methacryloyl group-containing polymerizable monomers, respectively.

Examples of polymerizable monomers which do not have an acidic group are as follows.

Monofunctional monomers: (meth)acrylic esters such as methyl(meth)acrylate, ethyl(meth)acrylate, butyl(meth)acrylate, hexyl(meth)acrylate, tetrahydrofurfuryl(meth)acrylate, 2-hydroxyethyl(meth)acrylate, glycidyl(meth)acrylate, lauryl(meth)acrylate, cyclohexyl(meth)acrylate, benzyl(meth)acrylate, allyl(meth)acrylate, 2-ethoxyethyl(meth)acrylate, methoxypolyethyleneglycol(meth)acrylate, glycerol(meth)acrylate, isobornyl(meth)acrylate, or the like; silane compounds such as γ-(meth)acryloyloxypropyl-trimethoxysilane, γ-(meth)acryloyloxypropyl-triethoxysilane, or the like; nitrogen-containing compounds such as 2-(N,N-dimethylamino) ethyl(meth)acrylate, N-methylol(meth)acrylamido, diacetone(meth)acrylamido, or the like.

Bifunctional aromatic monomers: 2,2-bis(4-(meth)acryloyloxyphenyl)propane, 2,2-bis(4-(3-(meth)acryloyloxy-2-hydroxypropoxy)phenyl)propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2(4-(meth)acryloyloxyethoxyphenyl)-2(4-(meth)acryloyloxydiethoxyphenyl)propane, 2(4-(meth)acryloyloxydiethoxyphenyl)-2(4-(meth)acryloyloxy-tri ethoxyphenyl)propane, 2(4-(meth)acryloyloxydipropoxyphenyl)-2(4-(meth)acryloyloxy-tr iethoxyphenyl)propane, 2,2-bis(4-(meth)acryloyloxydipropoxyphenyl)propane, 2,2-bis(4-(meth)acryloyloxyisopropoxyphenyl)propane, or the like.

Bifunctional aliphatic monomers: 2-hydroxy-3-acryloyloxypropylmethacrylate, hydroxypivalic acid neopentylglycol-di(meth)acrylate, ethyleneglycol-di(meth)acrylate, diethyleneglycol-di(meth)acrylate, triethyleneglycol-di(meth)acrylate, butyleneglycol-di(meth)acrylate, neopentylglycol-di(meth)acrylate, propyleneglycol-di(meth)acrylate, 1,3-butanediol-di(meth)acrylate, 1,4-butanediol-di(meth)acrylate, 1,6-hexanediol-di(meth)acrylate, glycelol-di(meth)acrylate, or the like, Trifunctional monomers: trimethylolpropane-tri(meth)acrylate, trimethylolethane-tri(meth)acrylate, trimethylolmethane tri(meth)acrylate, pentaerythritol-tri(meth)acrylate, or the like.

Tetrafunctional monomers: pentaerythritol tetra(meth)acrylate, ditrimethylolpropane tetra(meth)acrylate, or the like.

Specific example of the urethane polymerizable monomer includes bifunctional, trifunctional or more functional-di(meth)acrylate having urethane bond or the like. Such di(meth)acrylate is delivered from additional products which consists of polymerizable monomers having a hydroxy group and diisocyanate compounds. The polymerizable monomers described above include 2-hydroxyethyl(meth)acrylate, 2-hydroxypropyl(meth)acrylate, and 3-chloro-2-hydroxypropyl(meth)acrylate; and the diisocyanate compounds described above include methylcyclohexanediisocyanate, methylenebis(4-cyclohexylisocyanate), hexamethylenediisocyanate, trimethylhexamethylenediisocyanate, isophoronediisocyanate, diisocyanatemethylmethylbenzene, and 4,4-diphenylmethanediisocyanate.

Besides the (meth)acrylate polymerizable monomers described above, other polymerizable monomers that suit the purpose of the dental composition, e.g. a monomer having at least one or more polymerizable groups in a molecule, an oligomer, or a polymer, may be used without restriction. A substituent such as an acidic group or a fluoro group may be provided in the same molecule.

In the present invention, the polymerizable monomer is not necessarily of a single component, and may be a mixture of a plurality of polymerizable monomers. If the viscosity of the polymerizable monomer at room temperature is extremely high, or if the polymerizable monomer is solid, the polymerizable monomer is preferably combined with a polymerizable monomer with low viscosity to be used as a mixture of the polymerizable monomers. The combination is not limited to a combination of two kinds, and may be a mixture of three or more kinds. A polymer with only a monofunctional polymerizable monomer does not have a cross-linked structure, and generally tends to be inferior in mechanical strength of the polymer. Therefore, the monofunctional polymerizable monomer is preferably used together with a polyfunctional polymerizable monomer.

If adhesion to the tooth substance or a base metal is to be imparted to the dental curable composition according to the present invention, it is effective to use a polymerizable monomer containing in a molecule an acid group such as a phosphoric acid group, a carboxylic acid group, or a sulfonic acid group as a part or all of the polymerizable monomer. In order to improve adhesion to a precious metal, it is also effective for the purpose of the present invention to use a polymerizable monomer containing a sulfur atom in a molecule. Specific examples of the polymerizable monomer having adhesion are as follows.

Polymerizable monomers having a carboxylic group: (meth)acrylate, 1,4-di(meth)acryloyloxyethylpyromellitic acid, 6-(meth)acryloyloxynaphthalene-1,2,6-tricarbolic acid, N-(meth)acryloyl-p-aminobenzoate, N-(meth)acryloyl-5-aminosalycilic acid, 4-(meth)acryloyloxyethyl-trimellitic acid and anhydride thereof, 4-(meth)acryloyloxybutyl-trimellitic acid and anhydride thereof, 2-(meth)acryloyloxybenzoate, β-(meth)acryloyloxyethylhydrogensuccinate, β-(meth)acryloyloxyethylhydrogenmaleate, 11-(meth)acryloyloxy-1,1-undecane dicarboxylic acid, p-vinylbenzoate, or the like.

Monomers having a phosphate group: 2-(meth)acryloyloxyethyl-dihydrogenphosphate, 3-(meth)acryloyloxypropyl-dihydrogenphosphate, 10-(meth)acryloyloxydecyl-dihydrogenphosphate, bis(2-(meth)acryloyloxyethyl) hydrogenphosphate, 2-(meth)acryloyloxyethylphenylhydrogenphosphate, or the like.

Monomers having a sulfonate group: 2-(meth)acrylamido-2-methylpropanesulfonic acid, 4-(meth)acryloyloxybenzensulfonic acid, 3-(meth)acryloyloxypropanesulfonic acid, or the like.

Polymerizable monomers having a sulfur atom: (meth)acrylate having a triazinethiol group, (meth)acrylate having a mercapto group, (meth)acrylate having a polysulfide group, (meth)acrylate having a thiophosphate group, (meth)acrylate having a cyclic disulfide group, (meth)acrylate having a mercaptodithiazole group, (meth)acrylate having a thiouracil group, (meth)acrylate having a thiirane group, or the like. The polymerizable monomers may be used singly or in combination of two or more kinds thereof.

The content of the polymerizable monomer in the dental curable composition according to the present invention differs among materials used according to the use and the purpose, and therefore is not specifically limited. However, the content of the polymerizable monomer is preferably in the range of 5 to 50 wt % based on the entire dental curable composition for a composite resin, in the range of 5 to 90 wt % based on the entire dental curable composition for an adhesive, and in the range of 20 to 90 wt % based on the entire dental curable composition for a fissure sealant.

The polymerization initiator contained in the dental curable composition according to the present invention is not specifically limited, and a radical generator known in the art may be used without restriction.

The polymerization initiators are roughly divided into chemical polymerization initiators that are generally mixed immediately before use to initiate polymerization, thermal polymerization initiators that are heated or warmed to initiate polymerization, and photopolymerization initiators that are irradiated with light to initialize polymerization.

Examples of the chemical polymerization initiators include redox polymerization initiators formed from organic peroxide/amine compound or organic peroxide/amine compound/sulfinate, organic peroxide/amine compound/borate compound, and organic metal polymerization initiators that react with oxygen or water to initiate polymerization. Further, sulfinates and borate compounds may react with a polymerizable monomer having an acidic group to initiate polymerization.

Specific examples of the organic peroxide described above are as follows: benzoylperoxide, p-chlorobenzoylperoxide, 2,4-dichlorobenzoylperoxide, acetylperoxide, lauroylperoxide, tert-butylperoxide, cumenehydroperoxide, 2,5-dimethylhexan, 2,5-dihydroperoxide, methylethylketoneperoxide, tert-butylperoxybenzoate, or the like.

As the amine compounds described above, secondary amine or tertiary amine having an amine group coupled with an aryl group can be suitably used. Specific examples thereof are as follows: p-N,N-dimethyl-toluidine, N,N-dimethylaniline, N-β-hydroxyethyl-aniline, N,N-di(β-hydroxyethyl)-aniline, p-N,N-di(β-hydroxyethyl)-toluidine, N-methylaniline, p-N-methyl-toluidine, or the like.

Specific examples of the sulfinate include sodium benzenesulfinate, lithium benzenesulfinate, and sodium p-toluenesulfinate.

Examples of the borate compound include a sodium salt, a lithium salt, a potassium salt, a magnesium salt, a tetrabutylammonium salt, a tetramethylammonium salt, etc. of trialkyl phenyl borate and trialkyl (p-fluorophenyl) borate (in which the alkyl group is an n-butyl group, an n-octyl group, an n-dodecyl group, or the like).

Examples of the organic metal polymerization initiators include organic boron compounds such as triphenylborane, tributylborane, and partially oxidized tributylborane.

As the thermal polymerization initiators to be heated or warmed, azo compounds such as azobisisobutyronitrile, azobisisomethylbutyrate, and azobiscyanovalerate are suitably used besides the organic peroxides described above.

Meanwhile, the photopolymerization initiators may be formed from a photosensitizer, a photosensitizer/photopolymerization promoter, or the like.

Specific examples of the photosensitizer described above are as follows: α-diketones such as benzyl, camphorquinone, α-naphthyl, acetonaphthone, p,p'-dimethoxybenzyl, p,p'-dichlorobenzylacetyl, pentanedione, 1,2-phenanthrenequinone, 1,4-phenanthrenequinone, 3,4-phenanthrenequinone, 9,10-phenanthrenequinone, naphthoquinone, or the like; benzoinalkylethers such as benzoin, benzoinmethylether, benzomethylether, or the like; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone, 2,4-diisopropylthioxanthone, or the like; benzophenones such as benzophenone, p-chlorobenzophenone, p-methoxybenzophenone, or the like; acylphosphinoxide such as 2,4,6-trimethylbenzoyl-diphenylphosphinoxide, bis(2,6-dimethoxybenzoyl)-2,4,4-trimethylpentylphosphinoxide, or the like; α-aminoacetophenone such as 2-benzyl-dimethylamino-1-(4-morpholinophenyl)-butanone-1, 2-benzyl-diethylamino-1-(4-morpholinophenyl)-propanone-1, or the like; ketals such as benzyl-dimethylketal, benzyl-diethylketal, benzyl(2-methoxyethylketal), or the like; titanocene such as bis(cyclopentadienyl)-bis[2,6-difluoro-3-(1-pyrrolyl)phenyl]-titanium, bis(cyclopentadienyl)-bis(pentanefluorophenyl)-titanium, bis(cyclopentadienyl)-bis(2,3,5,6-tetrafluoro-4-disiloxyphenyl)-titanium, or the like.

Specific examples of the photopolymerization promoter described above are as follows: tertiary amines such as N,N-dimethylaniline, N,N-diethylaniline, N,N-di-n-butylaniline, N,N-dibenzylaniline, p-N,N-dimethyl-toluidine, m-N,N-dimethyl-toluidine, p-N,N-diethyl-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethylester, p-dimethylaminobenzoic acid aminoester, N,N-dimethylanthranilic acid methylester, N,N-dihydroxyethylaniline, p-N,N-dihydroxyethyl-toluidine, p-dimethylaminophenylalcohol, p-dimethylaminostyrene, N,N-dimethyl-3,5-xylidine, 4-dimethylaminopylidine, N,N-dimethyl-α-naphthylamine, N,N-dimethyl-β-naphthylamine, tributylamine, tripropylamine, triethylamine, N-methyl-diethanolamine, N-ethyl-diethanolamine, N,N-dimethylhexylamine, N,N-dimethyldodecylamine, N,N-dimethylstearylamine, N,N-dimethylaminoethylmethacrylate, N,N-diethylaminoethylmethacrylate, 2,2'-(n-butylimino)diethanol, or the like; secondary amines such as N-phenylglycine, or the like; barbituric acids such as 5-butyl barbituric acid, 1-benzyl-5-phenyl barbituric acid, or the like; tin compounds such as dibutyltin acetate, dibutyltin dilaurate, dioctyltin dilaurate, dioctyltin diverthatate, dioctyltin bis(mercaptoacetic acid isooctylester)salt, tetramethyl-1, 3-diacetoxy distannoxane, or the like; aldehyde compounds such as laurylaldehyde, terephthalaldehyde, or the like; sulfur containing compounds such as dodecylmercaptan, 2-mercaptobenzoxazole, 1-decanethiol, thiosalicylic acid, or the like.

In order to improve the photopolymerization promotion ability, it is effective to add oxycarboxylic acid such as citric acid, malic acid, tartaric acid, glycodic acid, gluconic acid, α-oxyisobutyric acid, 2-hydroxypropanoic acid, 3-hydroxypropanoic acid, 3-hydroxybutanoic acid, 4-hydroxybutanoic acid, dimethylolpropionic acid, or the like in addition to the photopolymerization promoter described above.

The polymerization initiators may be used singly or in combination of two or more kinds thereof. The polymerization initiators may be used in combination irrespective of the form of polymerization and the type of the polymerization initiators.

The content of the polymerization initiator may be selected as appropriate according to the use. In general, the content of the polymerization initiator may be selected from the range of 0.1 to 10 parts by weight based on the entire dental curable composition.

Among the polymerization initiators discussed above, the photopolymerization initiators that are irradiated with light to generate a radical are preferably used, and most suitably used to polymerize a dental composition with little air mixed in. Among the photopolymerization initiators, combinations of an α-diketone and a tertiary amine and an α-diketone and a tin compound are more preferable, and combinations of a camphorquinone and an aromatic amine in which an amino group of p-N,N-ethyl-dimethylaminobenzoate or the like is directly bonded to a benzene ring or an aliphatic amine in which a double bond is provided in a molecule of N,N-dimethylamino ethylmethacrylate or the like, and a camphorquinone and dibutyltin dilaurate are most preferable.

Besides, coumarin, cyanine, and thiazine sensitizing dyes, halomethyl group substituted-s-triazine derivatives, photo acid generators that generate a Bøonsted acid or a Lewis acid by irradiation with light such as diphenyliodonium salt compounds, quaternary ammonium halides, transition metal compounds, and so forth are also suitably used according to the use.

The filler contained in the dental curable composition according to the present invention is not specifically limited, and a filler known in the art such as an inorganic filler and/or an organic filler and/or an organic-inorganic composite filler, for example, may be used without restriction. The grain shape of the filler may be any shape like a sphere, a needle, a plate, a fracture, a scale, etc., and is not specifically limited. The type of the filler is also not specifically limited.

Specific examples of the inorganic filler include quartz, amorphous silica, aluminum silicate, aluminum oxide, titanium oxide, zirconium oxide, various types of glass (including glass obtained by a melting method, synthetic glass obtained by a sol-gel method, and glass generated by a gas phase reaction), calcium carbonate, talc, kaoline, clay, mica, aluminum sulfate, calcium sulfate, barium sulfate, calcium phosphate, hydroxyapatite, silicon nitride, aluminum nitride, titanium nitride, silicon carbide, boron carbide, calcium hydroxide, strontium hydroxide, and zeolite. Among these, aluminosilicate glass, borosilicate, aluminoborate, and boroaluminosilicate glass containing a heavy metal such as sodium, strontium, barium, and lanthanum are preferable. The average grain size of the inorganic filler is not specifically limited, and is preferably in the range of 0 to 10 μm, more preferably in the range of 0 to 5 μm.

Ultrafine particle inorganic fillers such as aerosil generated by a gas phase method or particles of silica-zirconia oxide generated from a solution in a sol-gel reaction may also be used. Cohesive inorganic fillers obtained by agglomerating such untrafine particles may also be used.

The organic filler can be obtained by polymerizing a monomer having a polymerizable group, and the type of the organic filler is not specifically limited. Specific examples of the organic filler include unsaturated aromatics such as styrene, α-methylstyrene, halogenated styrene, and divinylbenzene; unsaturated esters such as vinyl acetate and vinyl propionate; unsaturated nitriles such as acrylonitrile; and substances obtained by (co)polymerizing a single or a plurality of polymerizable monomers such as butadiene and isoprene. Substances obtained by polymerizing the polymerizable monomers discussed earlier known in the dental field are particularly preferable. The method of manufacturing the organic filler is not specifically limited, and may be any method in which the polymerizable monomer is subjected to an emulsion polymerization, a suspension polymerization, a dispersion polymerization, or the like, and may be a method in which a polymer bulk generated in advance is pulverized.

Organic-inorganic composite fillers in which inorganic particles are contained in an organic polymer may also be used. The inorganic particles to be contained in the organic polymer are not specifically limited, and those known in the art may be used. Examples of the inorganic particles include particles of the inorganic fillers discussed above. The method of manufacturing the organic-inorganic composite filler is also not specifically limited, and any method may be used. Examples of the method include a method in which the surfaces of the inorganic particles are microencapsulated or grafted with the organic substance, a method in which the inorganic particles are subjected to a radical polymerization after a polymerizable functional group or a polymerization initiating group is introduced into the surfaces of the inorganic particles, and a method in which a polymer bulk containing inorganic particles generated in advance is pulverized.

The average grain size of the organic filler or the organic-inorganic composite filler is preferably in the range of 1 to 100 μm, more preferably 3 to 50 μm, further more preferably 5 to 30 μm. The inorganic, organic, and organic-inorganic composite fillers may be used singly or in combination of several kinds thereof.

After the surfaces of the particles of the filler such the inorganic, organic, or organic-inorganic composite filler are treated by a method known in the art, the filler can be used for a dental composition. The surface treatment may be performed using a surfactant, fatty acid, organic acid, inorganic acid, a silane coupling agent, a titanate coupling agent, polysiloxane, or the like, for example. A preferable surface treatment method improves the wettability between the resin component and the surface of the filler and imparts superior properties to the dental composition, and can be selected as appropriate according to the required properties. The surface of the filler may be subjected, without restriction, to a surface treatment performed using a special surface treatment agent and/or by a special surface treatment method for the purpose of increasing the functionality of the filler.

The content of the filler in the dental curable composition according to the present invention differs among materials used according to the use and the purpose, and therefore is not specifically limited. However, the content of the filler is preferably in the range of 5 to 80 wt % based on the entire dental curable composition for a composite resin, in the range of 1 to 50 wt % based on the entire dental curable composition for an adhesive, and in the range of 0.01 to 70 wt % based on the entire dental curable composition for a fissure sealant.

Besides the polymerizable monomer, a polymerization catalyst, and the filler, components such as an ultraviolet absorbent such as 2-hydroxy-4-methylbenzophenone, a polymerization inhibitor such as hydroquinone, hydroquinone monomethyl ether, and 2,5-ditertiarybutyl-4-methylphenol, a discoloration inhibitor, an antibacterial material, a fluorine sustained release material, a ion sustained release material, a coloring pigment, and other additives known in the art may be added as necessary and as desired to the dental curable composition according to the present invention.

The packing form of the dental curable composition according to the present invention is not specifically limited, and may be selected as appropriate according to the use. The dental curable composition according to the present invention may be packed in one pack, two packs, or other packing forms according to the type or the purpose of use of the polymerization initiator.

EXAMPLES

The present invention will be specifically described in more detail below by way of examples. However, the present invention is not limited to such examples.

The performance of the dental curable compositions according to the examples was evaluated by the following methods.

1. Evaluation of Bending Strength

Purpose of evaluation: To evaluate the bending strength of the dental composition specimen Method of evaluation: A prepared dental composition was charged into a mold made of stainless steel, cover glasses were placed on both sides of the mold and pressed using a glass slab, and light irradiation was performed at five locations on the front surface for 30 seconds per location using a photopolymerization irradiator (Grip Light II manufactured by Shofu Inc.) to cure the composition. After the cured composition was taken out of the mold, light irradiation was performed in the same manner on the back surface to obtain a specimen (in a rectangular parallelepiped shape of 25×2×2 mm). The specimen was immersed in water at 37° C. for 24 hours, and subjected to a bending test. The bending test was conducted with a distance between supports of 20 mm and at a crosshead speed of 1 mm/min using an Instron universal testing machine (Instron 5567 manufactured by Instron). The test was conducted for ten specimens, and the average value for the ten specimens was evaluated.

2. Evaluation of Fluorescence Under Irradiation with Visible Light

Purpose of evaluation: To evaluate the fluorescence of the dental composition specimen under irradiation with visible light Method of evaluation: A prepared dental composition was charged into a mold made of stainless steel, cover glasses were placed on both sides of the mold and pressed using a glass slab, and light irradiation was performed at six locations for 30 seconds per location using a photopolymerization irradiator (Grip Light II manufactured by Shofu Inc.) to cure the composition. The cured composition was taken out of the mold to obtain a specimen (in a disc shape of Φ15×1 mm). The fluorescence of the specimen was evaluated with the eyes while the specimen was irradiated with visible light by a blue LED irradiator (BlueShot manufactured by Shofu Inc.). An optical filter that cuts off light included in a wavelength range of less than 550 nm was attached to the blue LED irradiator, and the fluorescence was evaluated by examining fluorescence that passed through the optical filter under irradiation of visible light with the eyes.

3. Evaluation of Aesthetics Under Natural Light

Purpose of evaluation: To evaluate the aesthetics of the dental composition specimen under natural light Method of evaluation: The aesthetics of the specimen prepared in 2. above was evaluated under natural light with the eyes.

[Criteria for Evaluation of Aesthetics Under Natural Light]

○: The aesthetics such as the color tone was not affected. No coloration was observed with the eyes in daily life (under natural light).

Δ: The aesthetics such as the color tone was not affected. However, slight coloration was observed with the eyes in daily life (under natural light).

x: The aesthetics such as the color tone was affected. Coloration was observed with the eyes in daily life (under natural light).

[Criteria for Evaluation of Fluorescence Under Irradiation with Visible Light]

○: Fluorescence was observed. Presence of fluorescence was clearly observed with the eyes during irradiation by the BlueShot (manufactured by Shofu Inc.).

Δ: Slight fluorescence was observed. Presence of some fluorescence was observed with the eyes during irradiation by the BlueShot (manufactured by Shofu Inc.).

x: No fluorescence was observed. Presence of fluorescence was not observed with the eyes during irradiation by the BlueShot (manufactured by Shofu Inc.).

[Raw Materials Used in Dental Curable Composition According to Examples of the Invention]

Bis-GMA: 2,2-bis(4-(3-methacryloyloxy-2-hydroxypropoxy)phenyl)propane,

UDMA: 2,2-bis(4methacryloyloxyethoxyphenyl)propane,

TEGDMA: triethyleneglycol-di(meth)acrylate,

HEMA: 2-hydroxyethyl methacrylate,

R-972: Aerosil R-972

CQ: camphorquinone,

Tin: dibutyltin dilaurate,

Sample 1: YAG: Ce doped fluorescent substance,

Sample 2: YAG: Ce undoped substance,

Sample 3: fluorescent substance of diethyl-1,2,5-dihydroxy-terephthalate,

Glass filler: manufactured as follows

[Manufacture of Glass Filler]

43 Parts by weight of silica, 20 parts by weight of aluminum oxide, 5 parts by weight of sodium fluoride, 10 parts by weight of calcium fluoride, 5 parts by weight of calcium phosphate, and 17 parts by weight of strontium carbonate were sufficiently mixed, and fused in a high-temperature elema furnace at 1400° C. to obtain glass. The glass was finely pulverized (to an average grain size of 3 μm) using a ball mill and a vibration mill, and subjected to a surface treatment performed using 3-methacryloyloxypropylmethoxysilane to obtain a raw material of the dental curable composition to be used in the examples.

Examples 1 to 9 and Comparative Examples 1 to 3

The raw materials were mixed at the preparation ratios shown in Table 1 and Table 2, kneaded, and defoamed to prepare pasty dental curable compositions 1 to 12 (the dental curable compositions 1 to 9 correspond to Examples 1 to 9, and the dental curable compositions 9 to 12 correspond to Comparative Examples 1 to 3).

The prepared dental curable compositions 1 to 12 were subjected to the evaluation methods discussed above to be examined for the bending strength, the visual recognizability under natural light, and the visual recognizability (fluorescence) under irradiation with visible light. The test results are shown in Table 1 and Table 2.

TABLE 1

| | Component name | Ex. 1 Dental curable composition 1 | Ex. 2 Dental curable composition 2 | Ex. 3 Dental curable composition 3 | Ex. 4 Dental curable composition 4 | Ex. 5 Dental curable composition 5 | Ex. 6 Dental curable composition 6 | Ex. 7 Dental curable composition 7 |
|---|---|---|---|---|---|---|---|---|
| Polymerizable monomer | Bis-GMA | 45.0 | — | 45.0 | 45.0 | 45.0 | 45.0 | 45.0 |
| | UDMA | — | 35.0 | — | — | — | — | — |
| | TEGDMA | 6.0 | 10.0 | 6.0 | 6.0 | 6.0 | 6.0 | 6.0 |
| | HEMA | 9.0 | 25.0 | 9.0 | 9.0 | 9.0 | 9.0 | 9.0 |
| Filler | Glass filler | 40.0 | 30.0 | 40.0 | 40.0 | 40.0 | 40.0 | 40.0 |
| | R-972 | 1.4 | 1.4 | 1.4 | 1.4 | 1.4 | 1.4 | 1.4 |
| Polymerization catalyst | CQ | 0.6 | 0.7 | 0.6 | 0.6 | 0.6 | 0.6 | 0.6 |
| | Tin | 1.2 | 1.4 | 1.2 | 1.2 | 1.2 | 1.2 | 1.2 |
| | Sample 1 | 0.1 | 0.1 | 0.05 | 5.0 | 20.0 | 0.01 | 0.001 |
| Evaluation of properties | Bending strength (MPa) | 100.5 | 98.5 | 99.8 | 101.5 | 101.5 | 97.6 | 83.4 |
| | Aesthetics with eyes | ○ | ○ | ○ | ○ | Δ | ○ | ○ |
| | Fluorescence under irradiation with visible light | ○ | ○ | ○ | ○ | ○ | ○ | Δ |

TABLE 2

| | Component name | Ex. 8 Dental curable composition 8 | Ex. 9 Dental curable composition 9 | Com. Ex. 1 Dental curable composition 10 | Com. Ex. 2 Dental curable composition 11 | Com. Ex. 3 Dental curable composition 12 | Cont. Ex. Teethmate (manufactured by Kuraray Noritake Dental Inc.) |
|---|---|---|---|---|---|---|---|
| Polymerizable monomer | Bis-GMA | 45.0 | 45.0 | 45.0 | 45.0 | 45.0 | — |
| | UDMA | — | — | — | — | — | — |
| | TEGDMA | 6.0 | 6.0 | 6.0 | 6.0 | 6.0 | — |
| | HEMA | 9.0 | 9.0 | 9.0 | 9.0 | 9.0 | — |
| Filler | Glass filler | 40.0 | 40.0 | 40.0 | 40.0 | 40.0 | — |
| | R-972 | 1.4 | 1.4 | 1.4 | 1.4 | 1.4 | — |
| Polymerization catalyst | CQ | 0.6 | 0.6 | 0.6 | 0.6 | 0.6 | — |
| | Tin | 1.2 | 1.2 | 1.2 | 1.2 | 1.2 | — |
| | Sample 1 | 0.1 | 0.1 | — | — | — | — |
| | Sample 2 | 0.1 | — | — | 0.1 | — | — |
| | Sample 3 | — | 0.1 | — | — | 0.1 | — |
| Evaluation of properties | Bending strength (MPa) | 98.2 | 100.2 | 80.5 | 81.4 | 84.0 | 83.0 |
| | Aesthetics with eyes | ○ | ○ | ○ | ○ | ○ | ○ |
| | Fluorescence under irradiation with visible light | ○ | ○ | x | x | x | x |

For Examples 1 to 9, as shown in Table 1 and Table 2, the bending strength was found to be improved compared to Comparative Example 1. In addition, the aesthetics under natural light was not affected, and fluorescence under irradiation with visible light was observed so that the dental curable compositions could be distinguished from the tooth substance. For Examples 1 to 4, 6, and 7 (with a content of Sample 1 in the range of 0.001 to 5.0 wt %), the aesthetics under natural light was found to be maintained.

Further, as shown in Table 1, fluorescence under irradiation with visible light was clearly observed for Examples 1 to 6, but only slightly observed for Example 7. That is, it was revealed that the content of Sample 1 (the fluorescent substance in the present invention was preferably determined to be 0.01 to 20 wt % based on the dental curable composition if high fluorescence (visual recognizability) under irradiation with visible light was required.

Further, as shown in Table 1, the bending strength was 98 MPa or more for Examples 1 to 5, but less than 98 MPa for Examples 6 and 7. That is, it was revealed that the content of Sample 1 (the fluorescent substance in the present invention) was preferably determined to be 0.1 to 20 wt % based on the dental curable composition if high mechanical strength was required.

In contrast to Example 1, none of Comparative Example 2 [in which a compound having a garnet structure but not doped with a rare-earth element (Sample 2) was used] and Comparative Example 3 [in which a fluorescent substance according to the related art not having a garnet structure (Sample 3) was used] were found to be fluorescent when irradiated by the BlueShot.

Comparison between Example 1 and Example 2 revealed that the bending strength, the aesthetics under natural light, and the fluorescence under irradiation with visible light or a visible ray were maintained even if the type of the polymerizable monomer was changed. Comparison between Example 1 and Examples 8 and 9 revealed that the bending strength, the aesthetics, and the fluorescence were maintained in the presence of Sample 1 even if other samples [a compound having a garnet structure but not doped with a rare-earth element (Sample 2) and a fluorescent substance according to the related art not having a garnet structure (Sample 3)] were mixed. The results indicate that the mechanical strength, the aesthetics, and the fluorescence properties are not easily affected even if components (such as impurities) other than the components of the present invention are mixed in the dental curable composition according to the present invention.

Control Example

The "Teethmate" manufactured by Kuraray Noritake Dental Inc. and available in the market was subjected to the evaluation methods discussed above as Control Example to be examined for the bending strength, the aesthetics under natural light, and the visual recognizability (fluorescence) under irradiation with visible light. Table 2 shows the test results. As shown in Table 1 and Table 2, Control Example was found to have low bending strength compared to Examples 1 to 9, and be not fluorescent under irradiation with visible light.

Although an embodiment of the present invention has been specifically described above, the present invention is not limited to the embodiment and the experimental examples. That is, conditions such as components and the amounts of additives described in the embodiment and the examples discussed above may be changed based on the technical concept of the present invention unless specifically stated otherwise.

Although the dental curable composition according to the present invention has a color tone that is similar to that of the tooth substance when seen with the eyes, the dental curable composition according to the present invention can be clearly distinguished from the tooth substance by irradiation with visible light. The presence of the dental curable composition according to the present invention can be identified by irradiation with visible light that is less harmful to living bodies. A device commonly used to cure a dental curable composition can also be used for irradiation with visible light, and therefore there is conveniently no need for a special device. Further, when irradiating the dental curable composition according to the present invention with visible light to cure the dental curable composition, polymerization of the polymerizable monomer inside the dental curable composition according to the present invention is promoted to improve the curability, which improves the hardness and the bending strength in particular, because the dental curable composition contains a fluorescent substance that absorbs visible light.

As has been described above, the dental curable composition according to the embodiment is a non-conventional dental curable composition in which a small amount of a fluorescent substance is used to generate extremely high fluorescence. Thus, use of the dental curable composition according to the present invention for a fissure sealant, for example, enables easily checking the status of filling minute spaces such as pits and fissures (e.g. whether the sealant is peeled off or chipped after the filling) with the eyes. Meanwhile, use of the dental curable composition according to the present invention as a dental orthodontic adhesive, for example, enables easily checking the presence of even a tiny amount of the adhesive remaining on the tooth surface after an orthodontic treatment.

What is claimed is:

1. A dental visible-light curable composition containing a fluorescent substance that generates fluorescence when irradiated with visible light, wherein:
   the fluorescent substance is a compound of formula (1) containing Ce, absorbs visible light with a peak wavelength in a wavelength range of 380 to 500 nm, and generates fluorescence with a peak wavelength in a wavelength range of 550 to 780 nm:

$$A_3B_2C_3O_{12} \tag{1}$$

where A, B, and C in formula (1) are a dodecahedral eight-coordinate Y element, an octahedral six-coordinate Al element, and a tetrahedral four-coordinate Al element, respectively;
   the content of the fluorescent substance is 0.01 to 5.0 wt %;
   the compound of formula (1) is a compound having a garnet structure; and the fluorescent substance is the compound doped with Ce.

2. The dental visible-light curable composition according to claim 1, wherein
   the dental visible-light curable composition containing the fluorescent substance, absorbs visible light with a peak wavelength in a wavelength range of 380 to 500 nm and generates fluorescence with a peak wavelength in a wavelength range of 550 to 780 nm, the fluorescence being visually recognizable through an optical filter configured to block light with a peak wavelength in a wavelength range of less than 550 nm.

3. The dental visible-light curable composition according to claim 2, wherein the visible light is visible light emitted from a blue LED.

4. The dental visible-light curable composition according to claim 3, wherein the dental visible-light curable composition is used for a fissure sealant or an orthodontic adhesive.

5. The dental visible-light curable composition according to claim 2, wherein the dental visible-light curable composition is used for a fissure sealant or an orthodontic adhesive.

6. The dental visible-light curable composition according to claim 1, wherein the dental visible-light curable composition is used for a fissure sealant or an orthodontic adhesive.

* * * * *